US007399605B2

(12) United States Patent
De Francesco et al.

(10) Patent No.: US 7,399,605 B2
(45) Date of Patent: *Jul. 15, 2008

(54) METHOD FOR IDENTIFYING A HCV RNA-DEPENDENT RNA POLYMERASE INHIBITOR

(75) Inventors: Raffaele De Francesco, Rome (IT); Licia Tomei, Rome (IT); Sven-Erik Behrens, Weimar (DE)

(73) Assignee: Instituto Di Ricerche Di Biologia Molecolare P. Angeletti S.p.A., Rome (IT)

( * ) Notice: Subject to any disclaimer, the term of this patent is extended or adjusted under 35 U.S.C. 154(b) by 450 days.

This patent is subject to a terminal disclaimer.

(21) Appl. No.: 10/085,476

(22) Filed: Feb. 27, 2002

(65) Prior Publication Data

US 2002/0164722 A1   Nov. 7, 2002

Related U.S. Application Data

(63) Continuation of application No. 08/952,981, filed as application No. PCT/IT96/00106 on May 24, 1996, now Pat. No. 6,383,768.

(30) Foreign Application Priority Data

May 25, 1995   (IT)   .............................. RM95A0343

(51) Int. Cl.
  *C12Q 1/48*   (2006.01)
  *C12Q 1/68*   (2006.01)
  *C12N 9/12*   (2006.01)
(52) U.S. Cl. .............................. 435/15; 435/194; 435/6; 435/5; 435/91.3; 435/69.2
(58) Field of Classification Search .................... 435/15, 435/194, 6, 5, 91.3
  See application file for complete search history.

(56) References Cited

U.S. PATENT DOCUMENTS

| | | | |
|---|---|---|---|
| 5,981,247 A | 11/1999 | Hagedorn et al. | ........... 435/194 |
| 6,383,768 B1 * | 5/2002 | De Francesco et al. | ........ 435/15 |

FOREIGN PATENT DOCUMENTS

| | | |
|---|---|---|
| EP | 0 464 287 A1 | 12/1990 |
| EP | 0 463 848 A2 | 6/1991 |
| WO | WO 94/05809 | 3/1994 |
| WO | WO 95/22985 | 8/1995 |
| WO | WO 97/12033 | 4/1997 |

OTHER PUBLICATIONS

Al et al., Expression and characterization of the NS5B (RNA-dependent RNA polymerase) gene of hepatitis C virus, Hepatology, vol. 22, No. 4 Pt. 2, pp. 331A, 1995.

Tomei et al., NS3 is a serine protease required for processing of hepatitis C virus polyprotein, J. of Virology, vol. 67, No. 7, pp. 4017-4026, 1993.

Bartenschlager et al., Kinetic and structural analyses of hepatitis C virus polyprotein processing, J. of Virology, vol. 68, No. 8, pp. 5045-5055, 1994.

Lin et al., Hepatitis C virus NS3 serine proteinase trans-cleavage requirements and processing kinetics, J. of Virology, vol. 68, No. 12, pp. 8147-8157, 1994.

Miller et al., Hepatitis C virus shares amino acid sequence similarity with pestiviruses and flaviviruses as well as members of two plant virus supergroups, Proc. Natl. Acad. Sci. USA, vol. 87, pp. 2057-2061, 1990.

Behrens et al., Identification and properties of the RNA-dependent RNA polymerase of hepatitis C virus, The EMBO Journal, vol. 15, No. 1, pp. 12-22, 1996.

Bartholomeusz et al., Use of a flavivirus RNA-dependent RNA polymerase assay to investigate the antiviral activity of selected compounds, Antiviral Research, vol. 24, pp. 341-350, 1994.

Grun et al., Dissociation of NS5 from cell fractions containing west nile virus-specific polymerase activity, Journal of Virology, vol. 61, No. 11, pp. 3641-3644, 1987.

Chu et al., Characterization of kunjin virus RNA-dependent RNA polymerase: reinitiation of synthesis in vitro, Virology, vol. 157, pp. 330-337, 1987.

Grun et al., Characterization of west nile virus RNA-dependent RNA polymerase and cellular terminal adenylyl and uridylyl transferase in cell-free extracts, Journal of Virology, vol. 60, No. 3, pp. 1113-1124, 1986.

Bartholomeusz et al., Synthesis of dengue virus RNA in vitro: initiation and the involvement of proteins NS3 and NS5, Arch Virol, vol. 128, pp. 111-121, 1993.

Lohmann et al., Biochemical properties of hepatitis C virus NS5B RNA-dependent RNA polymerase and identification of amino acid sequence motifs essential for enzymatic activity, Journal of Virology, vol. 71, No. 11, pp. 8416-8428, 1997.

Chung, R. et al. "Identification and Characterization of a Hepatitis C Virus-Specific RNA-Dependent RNA Polymerase Activity From Extracts of Infected Liver Tissue", Hepatology, 1992, vol. 16, No. 4 Part 2, Abstract 350.

Grakoui, A. et al. "Expression and Identification of Hepatitis C Virus Polyprotein Cleavage Products", Journal of Virology, 1993, vol. 67, pp. 1385-1395.

Handschuh, G. et al. "Bacterial expression and purification of hepatitis C virus capsid proteins of different size", Journal of Hepatology, 1995, vol. 22, pp. 143-150.

(Continued)

*Primary Examiner*—Richard G Hutson
(74) *Attorney, Agent, or Firm*—Melissa B. Wenk; Sheldon O. Heber

(57) ABSTRACT

The present invention relates to the molecular biology and virology of the hepatitis C virus (HCV). An object of the present invention is a method to reproduce in vitro the RNA-dependent RNA polymerase activity of HCV that makes use of sequences contained in the HCV NS5B protein.

2 Claims, 3 Drawing Sheets

OTHER PUBLICATIONS

Kato, N. et al. "Molecular cloning of the human hepatitis C virus genome from Japanese patients with non-A, non-B hepatitis", 1990, vol. 87, pp. 9524-9528.

Matsurra, Y. et al. "The molecular biology of hepatitis C", Seminars in Virology, 1993, vol. 4, pp. 297-304.

Neufeld, K. et al. "Identification of Terminal Adenylyl Transferase Activity of the Poliovirus Polymerase 3Dpol", Journal of Virology, 1994, vol. 68, pp. 5811-5818.

Plotch, S. et al. "Purification and Properties of Poliovirus RNA Polymerase Expressed in *Escherichia coli*", Journal of Virology, 1989, vol. 63, pp. 216-225.

Shirai, M. et al. "Induction of Cytotoxic T Cells to a Cross-Reactive Epitope in the Hepatitis C Virus Nonstructural RNA Polymerase-Like Protein", Journal of Virology, 1992, vol. 66, pp. 4098-4106.

Takamizawa, A. et al. "Structure and Organization of the Hepatitis C Virus Genome Isolated from Human Carriers", Journal of Virology, 1991, vol. 65, pp. 1105-1113.

Tsutsumi, M. et al. "Detection of Antigens Related to Hepatitis C Virus RNA Encoding the NS5 Region in the Livers of Patients with Chronic Type C Hepatitis", Hepatology, 1994, vol. 19, pp. 265-272.

Chung, R. et al. "Parenterally Transmitted Hepatitis: Viruses, Vaccines, and Antiviral Therapy", Comprehensive Therapy, 1993, vol. 19, pp. 163-173.

Lide, D. "CRC Handbook of Chemistry and Physics", 81st Edition 200-2001, pp. 7-1.

* cited by examiner

P ETL = promoter of the gene coding for the PCNA protein

P PH = promoter of the polyhedrin gene

Amp = gene coding for the ß-lactamase enzyme (ampicillin resistence)

LacZ (ß-gal) = gene coding for the ß-galactosidase enzyme

Col E1 = pBR322 replication origin

Ø10 = bacteriophage T7 Ø10 promoter rbs = Shine-Dalgarno ribosome binding site

ATG = translation initiation site of the protein coded by the bacteriophage T7 gene 10

ß-lactamase = gene coding for the ß-lactamase enzyme (ampicillin resistance)

Col E1 = pBR322 repliation origin

METHOD FOR IDENTIFYING A HCV RNA-DEPENDENT RNA POLYMERASE INHIBITOR

The present application is a continuation of U.S. application Ser. No. 08/952,981, filed Mar. 23, 1998, now U.S. Pat. No. 6,383,768 which is the U.S national filing of PCT/IT96/00106, International filing date May 24, 1996 (published in English).

The present invention relates to the molecular biology and virology of the hepatitis C virus (HCV). More specifically, this invention has as its object the RNA-dependent RNA polymerase (RdRp) and the nucleotidyl terminal transferase (TNTase) activities produced by HCV, methods of expression of the HCV RdRp and TNTase, methods for assaying in vitro the RdRp and TNTase activities encoded by HCV in order to identify, for therapeutic purposes, compounds that inhibit these enzymatic activities and therefore might interfere with the replication of the HCV virus.

As is known, the hepatitis C virus (HCV) is the main etiological agent of non-A, non-B hepatitis (NANB). It is estimated that HCV causes at least 90% of post-transfusional NANB viral hepatitis and 50% of sporadic NANB hepatitis. Although great progress has been made in the selection of blood donors and in the immunological characterization of blood used for transfusions, there is still a high number of HCV infections among those receiving blood transfusions (one million or more infections every year throughout the world). Approximately 50% of HCV-infected individuals develop cirrhosis of the liver within a period that can range from 5 to 40 years. Furthermore, recent clinical studies suggest that there is a correlation between chronic HCV infection and the development of hepatocellular carcinoma.

HCV is an enveloped virus containing an RNA positive genome of approximately 9.4 kb. This virus is a member of the Flaviviridae family, the other embers of which are the flaviviruses and the pestiviruses. The RNA genome of HCV has recently been mapped. Comparison of sequences from the HCV genomes isolated in various parts of the world has shown that these sequences can be extremely heterogeneous. The majority of the HCV genome is occupied by an open reading frame (ORF) that can vary between 9030 and 9099 nucleotides. This ORF codes for a single viral polyprotein, the length of which can vary from 3010 to 3033 amino acids. During the viral infection cycle, the polyprotein is proteolytically processed into the individual gene products necessary for replication of the virus. The genes coding for HCV structural proteins are located at the 5'-end of the ORF, whereas the region coding for the non-structural proteins occupies the rest of the ORF.

The structural proteins consist of C (core, 21 kDa), E1 (envelope, gp37) and E2 (NS1, gp61). C is a non-glycosylated protein of 21 kDa which probably forms the viral nucleocapsid. The protein E1 is a glycoprotein of approximately 37 kDa, which is believed to be a structural protein for the outer viral envelope. E2, another membrane glycoprotein of 61 kDa, is probably a second structural protein in the outer envelope of the virus.

The non-structural region starts with NS2 (p24), a hydrophobic protein of 24 kDa whose function is unknown. NS3, a protein of 68 kDa which follows NS2 in the polyprotein, is predicted to have two functional domains: a serine protease domain in the first 200 amino-terminal amino acids, and an RNA-dependent ATPase domain at the carboxy terminus. The gene region corresponding to NS4 codes for NS4A (p6) and NS4B (p26), two hydrophobic proteins of 6 and 26 kDa, respectively, whose functions have not yet been clarified. The gene corresponding to NS5 also codes for two proteins, NS5A (p56) and NS5B (p65), of 56 and 65 kDa, respectively.

Various molecular biological studies indicate that the signal peptidase, a protease associated with the endoplasmic reticulum of the host cell, is responsible for proteolytic processing in the non-structural region, that is to say at sites C/E1, E1/E2 and E2/NS2. A virally-encoded protease activity of HCV appears to be responsible for the cleavage between NS2 and NS3. This protease activity is contained in a region comprising both part of NS2 and the part of NS3 containing the serine protease domain, but does not use the same catalytic mechanism. The serine protease contained in NS3 is responsible for cleavage at the junctions between S3 and NS4A, between NS4A and NS4B, between NS4B and NS5A and between NS5A and NS5B.

Similarly to other (+)-strand RNA viruses, the replication of HCV is thought to proceed via the initial synthesis of a complementary (−)-RNA strand, which serves, in turn, as template for the production of progeny (+)-strand RNA molecules. An RNA-dependent RNA polymerase (RdRp) has been postulated to be involved in both these steps. An amino acid sequence present in all the RNA-dependent RNA polymerases can be recognized within the NS5 region. This suggests that the NS5 region contains components of the viral replication machinery. Virally-encoded polymerases have traditionally been considered important targets for inhibition by antiviral compounds. In the specific case of HCV, the search for such substances has, however, been severely hindered by the lack of both a suitable model system of viral infection (e.g. infection of cells in culture or a facile animal model), and a functional RdRp enzymatic assay.

It has now been unexpectedly found that this important limitation can be overcome by adopting the method according to the present invention, which also gives additional advantages that will be evident from the following.

The present invention has as its object a method for reproducing in vitro the RNA-dependent RNA polymerase activity of HCV that makes use of sequences contained in the HCV NS5B protein. The terminal nucleotidyl transferase activity, a further property of the NS5B protein, can also be reproduced using this method. The method takes advantage of the fact that the proteins containing sequences of NS5B can be expressed in either eukaryotic or prokaryotic heterologous systems: the recombinant proteins containing sequences of NS5B, either purified to apparent homogeneity or present in extracts of overproducing organisms, can catalyse the addition of ribonucleotides to the 3'-termini of exogenous RNA molecules, either in a template-dependent (RdRp) or template-independent (TNTase) fashion.

The invention also extends to a new composition of matter, characterized in that it comprises proteins whose sequences are described in SEQ ID NO: 1 or sequences contained therein or derived therefrom. It is understood that this sequence may vary in different HCV isolates, as all the RNA viruses show a high degree of variability. This new composition of matter has the RdRp activity necessary to the HCV virus in order to replicate its genome.

The present invention also has as its object the use of this composition of matter in order to prepare an enzymatic assay capable of identifying, for therapeutic purposes, compounds that inhibit the enzymatic activities associated with NS5B, including inhibitors of the RdRp and that of the TNTase.

Up to this point a general description has been given of the present invention. With the aid of the following examples, a more detailed description of specific embodiments thereof will now be given, in order to give a clearer understanding of its objects, characteristics, advantages and method of operation.

Figure 3:
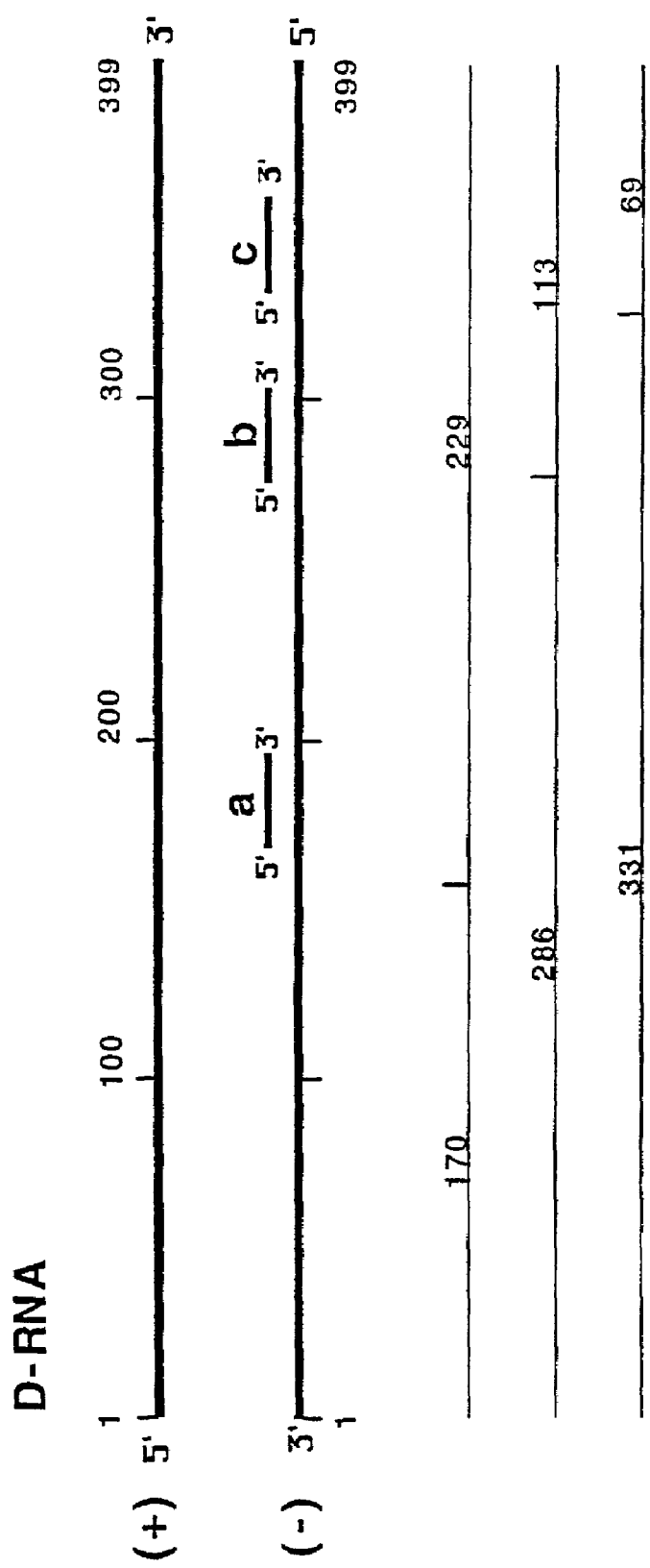

FIG. 3 shows a schematic drawing of (+) and (−) strands of D-RNA. The transcript contains the coding region of the DCoH mRNA. The DNA-oligonucleotides a, b and c were designed to anneal with the newly-synthesized antisense RNA and the DNA/RNA hybrid was subjected to cleavage with RNase H. The lower part of the scheme depicts the expected RNA fragment sizes generated by RNase digestion of the RNA (−) hybrid with oligonucleotides a, b and c, respectively.

DEPOSITS

*E. Coli* DH1 bacteria, transformed using the plasmids pBac 5B, pbac 25, pT7.7 DCoH and pT7.7NS5B—containing SEQ ID NO:1; SEQ ID NO:2; the cDNA for transcription of SEQ ID NO:12; and SEQ ID NO:1, respectively, filed on May 9, 1995 with The National Collections of Industrial and Marine Bacteria Ltd. (NCIMB), Aberdeen, Scotland, UK. under access numbers NCIMB 40727, 40728, 40729 and 40730, respectively.

EXAMPLE 1

Method of Expression of HCV RdRp/TNTase in *Spodoptera frugiperda* Clone 9 (Sf9) Cultured Cells.

Systems for expression of foreign genes in insect cultured cells, such as *Spodoptera frugiperda* clone 9 (Sf9) cells infected with baculovirus vectors are known in the art (V. A. Luckow, Baculovirus systems for the expression of human gene products, (1993) Current Opinion in Biotechnology 4, pp. 564-572). Heterologous genes are usually placed under the control of the strong polyhedrin promoter of the *Autographa californica* nuclear polyhedrosis virus of the *Bombix mori* nuclear polyhedrosis virus. Methods for the introduction of heterologous DNA in the desired site in the baculoviral vectors by homologous recombination are also known in the art (D. R. O'Reilly, L. K. Miller, V. A. Luckow, (1992), Baculovirus Expression Vectors-A Laboratory Manual, W. H. Freeman and Company, New York).

Figure 1:
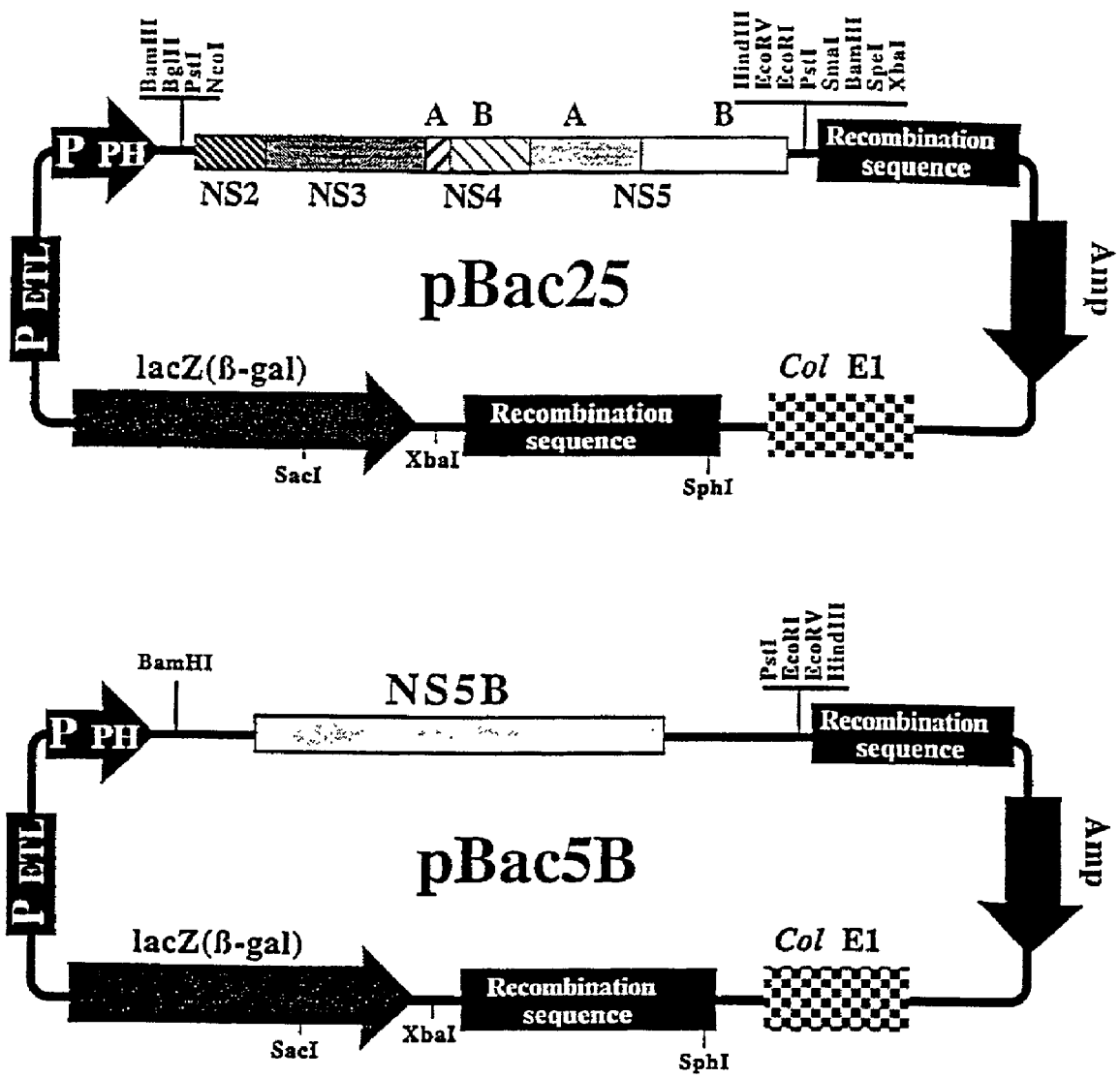
FIG. 1 shows the plasmids constructs used for the transfer of HCV cDNA into a baculovirus expression vector.

Plasmid vectors pBac5B and pBac25 are derivatives of a derivative of pBlueBacIII (Invitrogen) and were constructed for transfer of genes coding for NS4B and other non-structural HCV proteins in baculovirus expression vectors. The plasmids are schematically illustrated in FIG. 1 and their construction is described in detail in Example 8. Selected fragments of the cDNA corresponding to the genome of the HCV-BK isolate (HCV-BK; Takamizawa, A., Mori, C., Fuke, I., Manabe, S., Murakami, S., Fujita, J., Onishi, E., Andoh, T., Yoshida, I. and Okayama, H., (1991) Structure and Organization of the Hepatitis C Virus Genome Isolated from Human Carriers *J. Virol.*, 65, 1105-1113) were cloned under the strong polyhedrin promoter of the nuclear polyhedrosis virus and flanked by sequences that allowed homologous recombination in a baculovirus vector.

In order to construct pBac5B, a PCR product containing the cDNA region encoding amino acids 2420 to 3010 of the HCV polyprotein and corresponding to the NS5B protein (SEQ ID NO:1) was cloned between the BamHI and HindIII sites of pBlue BacIII. The PCR sense oligonucleotide contained a translation initiation signal, whereas the original HCV termination codon serves for translation termination.

pBac25 is a derivative of pBlueBacIII (Invitrogen) where the cDNA region coding for amino acids 810 to 3010 of the HCV-BK polyprotein (SEQ ID NO:2) was cloned between the NcoI and the HindIII restriction sites.

*Spodoptera frugiperda* clone 9 (Sf9) cells and baculovirus recombination kits were purchased from Invitrogen. Cells were grown on dishes or in suspension at 27° C. in complete Grace's insect medium (Gibco) containing 10% foetal bovine serum (Gibco). Transfection, recombination, and selection of baculovirus constructs were performed as recommended by the manufacturer. Two recombinant baculovirus clones, Bac25 and Bac5B, were isolated that contained the desired HCV cDNA.

For protein expression, Sf9 cells were infected either with the recombinant baculovirus Bac25 or Bac5B at a density of $2 \times 10^6$ cells per ml in a ratio of about 5 virus particles per cell. 48-72 hours after infection, the Sf9 cells were pelleted, washed once with phosphate buffered saline (PBS) and carefully resuspended ($7.5 \times 10^7$ cells per ml) in buffer A (10 mM Tris/Cl pH 8, 1.5 mM $MgCl_2$, 10 mM NaCl) containing 1 mM dithiothreitol (DTT), 1 mM phenylmethylsulphonyl-fluoride (PMSF, Sigma) and 4 mg/ml leupeptin. All the following steps were performed on ice: after swelling for 30 minutes, the cells were disrupted by 20 strokes in a Dounce homogeniser using a tight-fitting pestle. Glycerol, as well as the detergents Nonidet P-40 (NP40) and 3-[(3-Cholamidopropyl)-dimethyl-ammonio]-1-propanesulfonate (CHAPS), were added to final concentrations of 10% (v/v), 1% (v/v) and 0.5% /w/v), respectively, and the cellular extract was incubated for a further hour on ice with occasional agitation. The nuclei were pelleted by centrifugation for 10 minutes at 1000× g, and the supernatant was collected. The pellet was resuspended in buffer A containing the above concentrations of glycerol and detergents (0.5 ml per $7.5 \times 10^7$ nuclei) by 20 strokes in the Dounce homogeniser and then incubated for one hour on ice. After repelleting the nuclei, both supernatants were combined, centrifuged for 10 minutes at 8000× g and the pellet was discarded. The resulting crude cytoplasmic extract was used either directly to determine the RdRp activity or further purified on a sucrose gradient (see Example 5).

Infection of Sf9 cells with either the recombinant baculovirus Bac25 or Bac5B leads to the expression of the expected HCV proteins. Indeed, following infection of Sf9 cells with Bac25, correctly-processed HCV NS2 (24 kDa), NS3 (68 kDa), NS4B (26 kDa), NS4A (6 kDa), NS5A (56 kDa) and NS5B (65 kDa) proteins can be detected in the cell lysates by SDS-polyacrylamide gel electrophoresis (SDS-PAGE) and immunostaining. Following infection of Sf9 cells with Bac5B, only one HCV-encoded protein, corresponding in size to authentic NS5B (65 kDa), is detected by SDS-PAGE followed by immuno- or Coomassie Blue staining.

EXAMPLE 2

Method of Assay of Recombinant HCV RdRp on a Synthetic RNA Template/Substrate.

The RdRp assay is based on the detection of labelled nucleotides incorporated into novel RNA products. The in vitro assay to determine RdRp activity was performed in a total volume of 40 μl containing 1-5 μl of either Sf9 crude cytoplasmic extract or purified protein fraction. Unfractionated or purified cytoplasmic extracts of Sf9 cells infected with Bac25 or Bac5B may be used as the source of HCV RdRp. A Sf9 cell extract obtained from cells infected with a recombinant baculovirus construct expressing a protein that is not related to HCV may be used as a negative control. The following supplements are added to the reaction mixture (final concentrations): 20 mM Tris/Cl pH 7.5, 5 mM $MgCl_2$, 1 mM DTT, 25 mM KCl, 1 mM EDTA, 5-10 µCi [$^{32}$P] NTP of one species (unless otherwise specified, GTP, 3000 Ci/mmol, Amersham, was used), 0.5 mM each NTP (i.e. CTP, UTP, ATP unless specified otherwise), 20 U RNasin (Promega), 0.5 µg RNA-substrate (ca. 4 pmol; final concentration 100 nM), 2 µg actinomycin D (Sigma). The reaction was incubated for two hours at room temperature, stopped by the addition of an equal volume of 2× Proteinase K (PK, Boehringer Mannheim) buffer (300 mM NaCl, 100 mM Tris/Cl pH 7.5, 1% w/v SDS) and followed by half an hour of treatment with 50 µg of PK at 37° C. RNA products were PCA extracted, precipitated with ethanol and analysed by electrophoresis on 5% polyacrylamide gels containing 7M urea.

The RNA substrate we normally used for the assay (D-RNA) had the sequence reported in SEQ ID NO: 12, and was typically obtained by in vitro transcription of the linearized plasmid pT7-7(DCoH) with T7 polymerase, as described below.

Plasmid pT7-7(DCoH) (FIG. 2) was linearized with the unique BglII restriction site contained at the end of the DCoH coding sequence and transcribed in vitro with T7 polymerase (Stratagene) using the procedure described by the manufacturer. Transcription was stopped by the addition of 5 U/10 µl of DNaseI (Promega). The mixture was incubated for a further 15 minutes and extracted with phenol/chloroform/isoamylalcohol (PCA). Unincorporated nucleotides were removed by gel-filtration through a 1-ml Sephadex G50 spun column. After extraction with PCA and ethanol precipitation, the RNA was dried, redissolved in water and its concentration determined by optical density at 260 nm.

As will be clear from the experiments described below, any other RNA molecule other than D-RNA, may be used for the RdRp assay of the invention.

The above described HCV RdRp assay gave rise to a characteristic pattern of radioactively-labelled reaction products: one labelled product, which comigrated with the substrate RNA was observed in all reactions, including the negative control. This RNA species could also be visualised by silver staining and was thus thought to correspond to the input substrate RNA, labelled most likely by terminal nucleotidyl transferase activities present in cytoplasmic extracts of baculovirus-infected Sf9 cells. In the reactions carried out with the cytoplasmic extracts of Sf9 cells infected with either Bac25 or Bac5B, but not of cells infected with a recombinant baculovirus construct expressing a protein that is not related to HCV, an additional band was observed, migrating faster than the substrate RNA. This latter reaction product was found to be labelled to a high specific activity, since it could be detected solely by autoradiography and not by silver staining. This novel product was found to be derived from the externally-added RNA template, as it was absent from control reactions where no RNA was added. Interestingly, the formation of a labelled species migrating faster than the substrate RNA was consistently observed with a variety of template RNA molecules, whether containing the HCV 3'-untranslated region or not. The 399 nucleotide mRNA of the liver-specific transcription cofactor DCoH (D-RNA) turned out to be an efficiently accepted substrate in our RdRp assay.

In order to define the nature of the novel species generated in the reaction by the Bac25- or Bac5B-infected cell extracts, we carried out the following series of experiments. (i) The product mixture was treated with RNAse A or Nuclease P1. As this resulted in the complete disappearance of the radioactive bands, we concluded that both the labelled products were RNA molecules. (ii) Omission from the reaction mixtures of any of the four nucleotide triphosphates resulted in labelling of only the input RNA, suggesting that the faster migrating species is a product of a polymerisation reaction. (iii) Omission of $Mg^{2+}$ ions from the assay caused a complete block of the reaction: neither synthesis of the novel RNA nor labelling of the input RNA were observed. (iv) When the assay was carried out with a radioactively labelled input RNA and unlabelled nucleotides, the labelled product was indistinguishable from that obtained under the standard conditions. We concluded from this result that the novel RNA product is generated from the original input RNA molecule.

Taken together, our data demonstrate that the extracts of Bac25- or Bac5B-infected Sf9 cells contain a novel magnesium-dependent enzymatic activity that catalyses de novo RNA synthesis. This activity was shown to be dependent on the presence of added RNA, but independent of an added primer or of the origin of the input RNA molecule. Moreover, as the products generated by extracts of Sf9 cells infected with either Bac25 or Bac5B appeared to be identical, the experiments just described indicate that the observed RdRp activity is encoded by the HCV NS5B protein.

EXAMPLE 3

Methods for the Characterization of the HCV RdRp RNA Product

The following methods were employed in order to elucidate the structural features of the newly-synthesized RNA product. Under our standard electrophoresis conditions (5% polyacrylamide, 7M urea), the size of the novel RNA product appeared to be approximately 200 nucleotides. This could be due to either internal initiation of RNA transcription, or to premature termination. These possibilities, however, appeared to be very unlikely, since products derived from RdRp assays using different RNA substrates were all found to migrate significantly faster than their respective templates. Increasing the temperature during electrophoresis and the concentration of acrylamide in the analytical gel lead to a significantly different migration behaviour of the RdRp product. Thus, using for instance a gel system containing 10% acrylamide, 7M urea, where separation was carried out at higher temperature, the RdRp product migrated slower than the input substrate RNA, at a position corresponding to at least double the length of the input RNA. A similar effect was observed when RNA-denaturing agents such as methylhydroxy-mercury ($CH_3HgOH$, 10 mM) were added to the RdRp products prior to electrophoresis on a low-percentage/lower temperature gel. These observations suggest that the RdRp product possesses an extensive secondary structure.

We investigated the susceptibility of the product molecule to a variety of ribonucleases of different specificity. The product was completely degraded upon treatment with RNase A. On the other hand, it was found to be surprisingly resistant to single-strand specific nuclease RNase T1. The input RNA was completely degraded after 10 minutes incubation with 60 U RNase T1 at 22° C. and silver staining of the same gel confirmed that not only the template, but also all other RNA usually detectable in the cytoplasmic extracts of Sf9 cells was completely hydrolysed during incubation with RNase T1. In contrast, the RdRp product remained unaltered and was affected only following prolonged incubation with RNase T1.

Thus, after two hours of treatment with RNase T1, the labelled product molecule could no longer be detected at its original position in the gel. Instead, a new band appeared that had an electrophoretic mobility similar to the input template RNA. A similar effect was observed when carrying out the RNAse T1 digestion for 1 hour, but at different temperatures: at 22° C., the RdRp product remained largely unaffected whereas at 37° C. it was converted to the new product that co-migrates with the original substrate.

The explanation for these observations is that the input RNA serves as a template for the HCV RdRp, where the 3'-OH is used to prime the synthesis of the complementary strand by a turn-or "copy-back" mechanism to give rise to a duplex RNA "hairpin" molecule, consisting of the sense (template) strand to which an antisense strand is covalently attached. Such a structure would explain the unusual electrophoretic mobility of the RdRp product on polyacrylamide gels as well as its high resistance to single-strand specific nucleases. The turn-around loop should not be base-paired and therefore ought to be accessible to the nucleases. Treatment with RNase T1 thus leads to the hydrolysis of the covalent link between the sense and antisense strands to yield a double-stranded RNA molecule. During denaturing gel electrophoresis the two strands become separated and only the newly-synthesized antisense strand, which should be similar in length to the original RNA template, would remain detectable. This mechanism would appear rather likely, especially in view of the fact that this kind of product is generated by several other RNA polymerases in vitro.

The following experiment was designed in order to demonstrate that the RNA product labelled during the polymerase reaction and apparently released by RNase T1 treatment exhibits antisense orientation with respect to the input template. For this purpose, we synthesized oligodeoxyribonucleotides corresponding to three separate sequences of the input template RNA molecule (FIG. 2), oligonucleotide a, corresponding to nucleotides 170-195 of D-RNA (SEQ ID NO: 3); oligonucleotide b, complementary to nucleotides 286-309 (SEQ ID NO: 4); oligonucleotide c, complementary to nucleotides 331-354 (SEQ ID NO: 5) These were used to generate DNA/RNA hybrids with the product of the polymerase reaction, such that they could be subjected to RNase H digests. Initially, the complete RdRp product was used in the hybridizations. However, as this structure is too thermostable, no specific hybrids were formed. The hairpin RNA was therefore pre-treated with RNase T1, denatured by boiling for 5 minutes and then allowed to cool down to room temperature in the presence of the respective oligonucleotide. As expected, exposure of the hybrids to RNase H yielded specific cleavage products. Oligonucleotide a-directed cleavage lead to products of about 170 and 220 nucleotides in length, oligonucleotide b yielded products of about 290 and 110 nucleotides and oligonucleotide c gave rise to fragments of about 330 and 65 nucleotides. As these fragments have the expected sizes (see FIG. 3), the results indicate that the HCV NS5B-mediated RNA synthesis proceeds by a copy-back mechanism that generates a hairpin-like RNA duplex.

EXAMPLE 4

Method of Assay of Recombinant HCV TNTase on a Synthetic RNA Substrate

The TNTase assay is based on the detection of template-independent incorporation of labelled nucleotides to the 3' hydroxyl group of RNA substrates. The RNA substrate for the assay (D-RNA) was typically obtained by in vitro transcription of the linearized plasmid pT7-7DCOH with T7 polymerase as described in Example 2. However, any other RNA molecule, other than D-RNA, may be used for the TNTase assay of the invention.

The in vitro assay to determine TNTase activity was performed in a total volume of 40 μl containing 1-5 μl of either Sf9 crude cytoplasmic extract or purified protein fraction. Unfractionated or purified cytoplasmic extracts of Sf9 cells infected with Bac25 or Bac5B may be used as the source of HCV TNTase. An Sf9 cell extract obtained from cells infected with a recombinant baculovirus construct expressing a protein that is not related to HCV may be used as a negative control. The following supplements are added to the reaction mixture (final concentrations): 20 mM Tris/Cl pH 7.5, 5 mM $MgCl_2$, 1 mM DTT, 25 mM KCl, 1 mM EDTA, 5-10 μCi [$^{32}$P] NTP of one species (unless otherwise specified, UTP, 3000 Ci/mmol, Amersham, was used), 20 U RNasin (Promega), 0.5 μg RNA-substrate (ca. 4 pmol; final concentration 100 nM), 2 μg actinomycin D (Sigma). The reaction was incubated for two hours at room temperature, stopped by the addition of an equal volume of 2× Proteinase K (PK, Boehringer Mannheim) buffer (300 mM NaCl, 100 mM Tris/Cl pH 7.5, 1% w/v SDS) and followed by half an hour of treatment with 50 μg of PK at 37° C. RNA products were PCA extracted, precipitated with ethanol and analysed by electrophoresis on 5% polyacrylamide gels containing 7M urea.

EXAMPLE 5

Method for the Purification of the HCV RdRp/TNTase by Sucrose Gradient Sedimentation A linear 0.3-1.5 M sucrose gradient was prepared in buffer A containing detergents (see Example 1). Up to 2 ml of extract of Sf9 cells infected with Bac5B or Bac25 (corresponding to about 8×10$^7$ cells) were loaded onto a 12 ml gradient. Centrifugation was carried out for 20 hours at 39000× g using a Beckman SW40 rotor. 0.5 ml fractions were collected and assayed for activity. The NS5B protein, identified by western blotting, was found to migrate in the density gradients with an unexpectedly high sedimentation coefficient. The viral protein and ribosomes were found to co-sediment in the same gradient fractions. This unique behaviour enabled us to separate the viral protein from the main bulk of cytoplasmic proteins, which remained on the top of the gradient. The RdRp activity assay revealed that the RdRp activity co-sedimented with the NS5B protein. A terminal nucleotidyl transferase activity (TNTase) was also present in these fractions.

EXAMPLE 6

Method for the Purification of the HCV TNTase/RdRp from Sf9 Cells

Whole cell extracts are made from 1 g of Sf9 cells infected with Bac5B recombinant baculovirus. The frozen cells are thawed on ice in 10 ml of buffer containing 20 mM Tris/HCl pH 7.5, 1 mM EDTA, 10 mM DTT, 50% glycerol (N buffer) supplemented with 1 mM PMSF. Triton X-100 and NaCl are then added to a final concentration of 2% and 500 mM, respectively, in order to promote cell breakage. After the addition of $MgCl_2$ (10 mM) and DNase I (15 μg/ml), the mixture is stirred at room temperature for 30 minutes. The extract is then cleared by ultracentrifugation in a Beckman centrifuge, using a 90 Ti rotor at 40,000 rpm for 30 minutes at 4° C. The cleared extract is diluted with a buffer containing 20 mM Tris/HCl pH 7.5, 1 mM EDTA, 10 mM DTT, 20% glycerol, 0.5% Triton X-100 (LG buffer) in order to adjust the NaCl concentration to 300 mM and incubated batchwise with 5 ml of DEAE-Sepharose Fast Flow, equilibrated in LG buffer containing 300 mM NaCl. The matrix is then poured into a column and washed with two volumes of the same buffer. The flow-through and the first wash of the DEAE-Sepharose Fast Flow column is diluted 1:3 with LG buffer and applied onto a Heparin-Sepharose CL6B column (10 ml) equilibrated with LG buffer containing 100 mM NaCl. The Heparin-Sepharose CL6B is washed thoroughly and the bound proteins are eluted with a linear 100 ml gradient, from 100 mM to 1M NaCl in buffer LG. The fractions containing NS5B, as judged by silver- and immuno-staining of SDS-PAGE, are pooled and diluted with LG buffer in order to adjust the NaCl concentration to 50 mM. The diluted fractions are subsequently applied to a Mono Q-FPLC column (1 ml) equilibrated with LG buffer containing 50 mM NaCl. Proteins are eluted with a linear gradient (20 ml) from 50 mM to 1M NaCl in LG buffer. The fractions containing NS5B, as judged by silver- and immuno-staining of SDS-PAGE, are pooled and dialysed against LG buffer containing 100 mM NaCl. After extensive dialysis, the pooled fractions were loaded onto a PoyU-Sepharose CL6B (10 ml) equilibrated with LG buffer containing 100 mM NaCl. The PoyU-Sepharose CL6B was washed thoroughly and the bound proteins were eluted with a linear 100 ml gradient, from 100 mM to 1M NaCl in buffer LG. The fractions containing NS5B, as judged by silver- and immuno-staining of SDS-PAGE, are pooled, dialysed against LG buffer containing 100 mM NaCl and stored in liquid nitrogen prior to activity assay.

Fractions containing the purified protein NS5B were tested for the presence of both activities. The RdRp and TNTase activities were found in the same fractions. These results indicate that both activities, RNA-dependent RNA polymerase and terminal ribonucleotide transferase are the functions of the HCV NS5B protein.

We tested the purified NS5B for terminal nucleotidyl transferase activity with each of the four ribonucleotide triphosphates at non-saturating substrate concentrations. The results clearly showed that UTP is the preferred TNTase substrate, followed by ATP, CTP and GTP irrespective of the origin of the input RNA.

EXAMPLE 7

Method of Assay of Recombinant HCV RdRp on a Homopolymeric RNA Template

Thus far we have described that HCV NS5B possesses an RNA-dependent RNA polymerase activity and that the synthesis of complementary RNA strand is a template-primed reaction. Interestingly, using unfractionated cytoplasmic extracts of Bac5B or Bac25 infected Sf9 cells as a source of RdRp we were not able to observe complementary strand RNA synthesis that utilized an exogenously added oligonucleotide as a primer. We reasoned that this could be due to the abundant ATP-dependent RNA-helicases that would certainly be present in our unfractionated extracts. We therefore wanted to address this question using the purified NS5B.

First of all, we wanted to establish whether the purified NS5B polymerase is capable of synthesizing RNA in a primer-dependent fashion on a homopolymeric RNA template: such a template should not be able to form intramolecular hairpins and therefore we expected that complementary strand RNA synthesis be strictly primer-dependent. We thus measured UMP incorporation dependent on poly(A) template and evaluated both oligo(rU)$_{12}$ and oligo(dT)$_{12-18}$ as primers for the polymerase reaction. Incorporation of radioactive UMP was measured as follows. The standard reaction (10-100 μl) was carried out in a buffer containing 20 mM Tris/HCl pH 7.5, 5 mM MgCl$_2$, 1 mM DTT, 25 mM KCl, 1 mM EDTA, 20 U RNasin (Promega), 1 μCi [$^{32}$P] UTP (400 Ci/mmol, Amersham) or 1 μCi [$^3$H] UTP (55 Ci/mmol, Amersham), 10 μM UTP, and 10 μg/ml poly(A) or poly(A)/oligo (dT)$_{12-18}$. Oligo(U)$_{12}$ (1 μg/ml) was added a primer. Poly A and polyA/oligodT$_{12-18}$ were purchased from Pharmacia. Oligo(U)$_{12}$ was obtained from Genset. The final NS5B enzyme concentration was 10-100 nM. Under these conditions the reaction procedeed linearly for up to 3 h hours. After 2 hours of incubation at 22_, the reaction was stopped by applying the samples to DE81 filters (Whatman), the filters washed thoroughly with 1M Na$_2$HPO$_4$/NaH$_2$PO$_4$, pH 7.0, rinsed with water, air dried and finally the filter-bound radioactivity was measured in a scintillation β-counter. Alternatively, the in vitro-synthesized radioactive product was precipitated by 10% trichloroacetic acid with 100 μg of carrier tRNA in 0.2 M sodium pyrophosphate, collected on 0.45-μm Whatman GF/C filters, vacuum dried, and counted in scintilaltion fluid.

Although some [$^{32}$P]UMP or [$^3$H]UMP ncorporation was detectable even in the absence of a primer and is likely to be due to the terminal nucleotidyl transferase activity associated with our purified NS5B, up to 20% of product incorporation was observed only when oligo(rU)$_{12}$ was included as primer in the reaction mixture. Unexpectedly, also oligo(dT)$_{12-18}$ could function as a primer of poly(A)-dependent poly(U) synthesis, albeit with a lower efficiency.

Other template/primers suitable for measuring the RdRp activity of NS5B include poly(C)/oligo(G) or poly(C)/oligo (dG) in the presence of radioactive GTP, poly(G)/oligo(C) or poly(G)/oligo(dC) in the presence of radioactive CTP, poly (U)/oligo(A) or poly(U)/oligo(dA) in the presence of radioactive ATP, poly(I)/oligo(C) or poly(I)/oligo(dC) in the presence of radioactive CTP.

EXAMPLE 8

Method of Expression of HCV RdRp/TNTase in E. Coli

Figure 2:
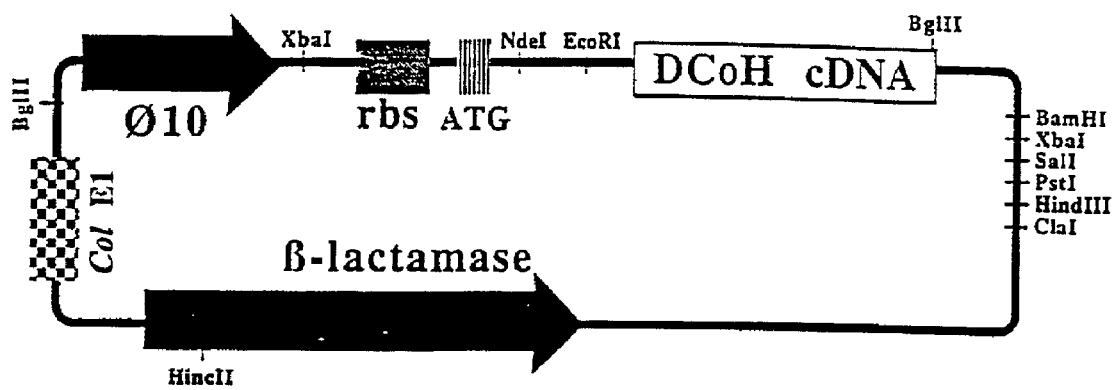
FIG. 2 shows the plasmids used for the in vitro synthesis of the D-RNA substrate of the HCV RNA-dependent RNA polymerase [pT7-7(DCoH)], and for the expression of the HCV RNA-dependent RNA polymerase in *E. coli* cells [pT7-7 (NS5B)], respectively.
Figure 2:
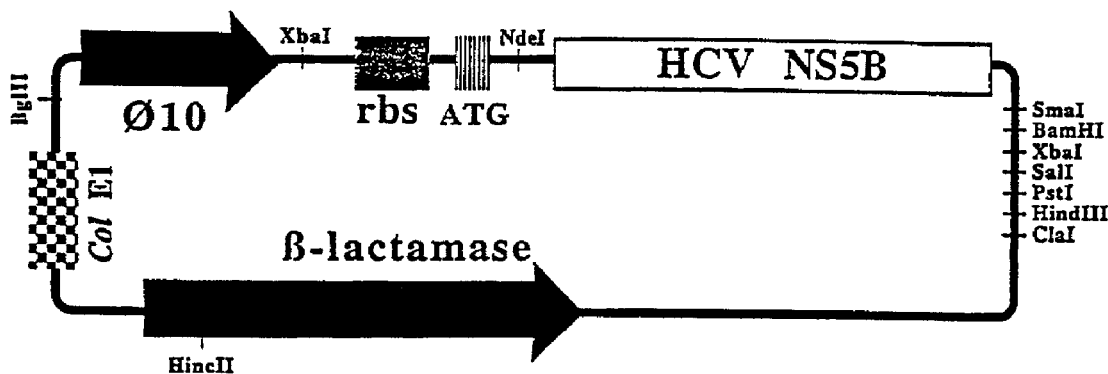

The plasmid pT7-7(NS5B), described in FIG. 2 and Example 8, was constructed in order to allow expression in E. coli of the HCV protein fragment having the sequence reported in SEQ ID NO 1. Such protein fragment contains the RdRp and the TNTase of NS5B, as discussed above. The fragment of HCV CDNA coding for the NS5B protein was thus cloned downstream of the bacteriophage T7 Ø10 promoter and in frame with the first ATG codon of the phage T7 gene 10 protein, usig methods that are known to the molecular biology practice and described in detail in Example 8. The pT7-7(NS5B) plasmid also contains the gene for the b-lactamase enzyme that can be used as a marker of selection of E. coli cells transformed with plasmid pT7-7(NS5B).

The plasmid pT7-7(NS5B) was then transformed in the E. coli strain BL21(DE53), which is normally employed for high-level expression of genes cloned into expression vectors containing T7 promoter. In this strain of E. coli, the T7 gene polymerase is carried on the bacteriophage 1 DE53, which is integrated into the chromosome of BL21 cells (Studier and Moffatt, Use of bacteriophage T7 RNA polymerase to direct selective high-level expression of cloned genes, (1986), J. Mol. Biol. 189, p. 113-130). Expression from the gene of interest is induced by addition of isopropylthiogalactoside (IPTG) to the growth medium according to a procedure that has been previously described (Studier and Moffatt, 1986). The recombinant NS5B protein fragment containing the RdRp is thus produced in the inclusion bodies of the host cells. Recombinant NS5B protein can be purified from the particulate fraction of E. coli BL21(DE53) extracts and refolded according to procedures that are known in the art (D. R. Thatcher and A. Hichcok, Protein folding in Biotechnology (1994) in "Mechanism of protein folding" R. H. Pain EDITOR, IRL PRESS, p.229-255). Alternatively, the recombinant NS5B protein could be produced as soluble protein by lowering the temperature of the bacterial growth media below 20_C. The soluble protein could thus be purified from lysates of E. coli substantially as described in Example 5.

EXAMPLE 9

Detailed Construction of the Plasmids in Figures

Selected fragments of the cDNA corresponding to the genome of the HCV-BK isolate (HCVBK) were cloned under the strong polyhedrin promoter of the nuclear polyhedrosis virus and flanked by sequences that allowed homologous recombination in a baculovirus vector.

pBac5B contains the HCV-BK sequence comprised between nucleotide 7590 and 9366, and codes for the NS5B protein reported in SEQ ID NO: 1. In order to obtain this plasmid, a cDNA fragment was generated by PCR using synthetic oligonucleotides having the sequences 5'-AAG-GATCCATGTCAATGTCCTACACATGGAC-3' (SEQ ID NO: 6) and 5'-AATATTCGAATTCATCGGTTGGGGAG-CAGGTAGATG-3' (SEQ ID NO: 7), respectively. The PCR product was then treated with the Klenow DNA polymerase, digested at the 5'-end with BamHI, and subsequently cloned between the BamHI and SmaI sites of the Bluescript SK(+) vector. Subsequently, the cDNA fragment of interest was digested out with the restriction enzymes BamHI and HindIII and religated in the same sites of the pBlueBacIII vector (Invitrogen)

pBac25 is contains the HCV-BK cDNA region comprised between nucleotides 2759 and 9416 of and codes for amino acids 810 to 3010 of the HCV-BK polyprotein (SEQ ID NO: 2). This construct was obtained as follows. First, the 820 bp cDNA fragment containing the HCV-BK sequence comprised between nucleotides 2759 and 3578 was obtained from pCD(38-9.4) (Tomei L., Failla, C., Santolini, E., De Francesco, R. and La Monica, N. (1993) NS3 is a Serine Protease Required for Processing of Hepatitis C Virus Polyprotein J. Virol., 67 , 4017-4026) by digestion with NcoI and cloned in the NcoI site of the pBlueBacIII vector (Invitrogen) yielding a plasmid called pBacNCO. The cDNA fragment containing the HCV-BK sequence comprised between nucleotides 1959 and 9416 was obtained from pCD(38-9.4) (Tomei et al., 1993) by digestion with NotI and XbaI and cloned in the same sites of the Bluescript SK(+) vector yielding a plasmid called pBlsNX. The cDNA fragment containing the HCV-BK sequence comprised between nucleotides 3304 and 9416 was obtained from pBlsNX by digestion with SacII and HindIII and cloned in the same sites of the pBlsNX plasmid, yielding the pBac25 plasmid.

pT7-7(DCoH) contains the entire coding region (316 nucleotides) of the rat dimerization cofactor of hepatocyte nuclear factor-1a å (DCoH; Mendel, D. B., Khavari, P. A., Conley, P. B., Graves, M. K., Hansen, L. P., Admon, A. and Crabtree, G. R. (1991) Characterization of a Cofactor that Regulates Dimerization of a Mammalian Homeodomain Protein, Science 254, 1762-1767; GenBank accession number: M83740). The cDNA fragment corresponding to the coding sequence for rat DCOH was amplified by PCR using the synthetic oligonucleotide Dpr1 and Dpr2 that have the sequence TGGCTGGCAAGGCACACAGGCT (SEQ ID NO: 8) and AGGCAGGGTAGATCTATGTC (SEQ ID NO: 9), respectively. The cDNA fragment thus obtained was cloned into the SmaI restriction site of the E. coli expression vector pT7-7. The pT7-7 expression vector is ea derivative of pBR322 that contains, in addition to the β-lactamase gene and the Col E1 orifgin of replication, the T7 polymerase promoter Ø10 and the translational start site for the T7 gene 10 protein (Tabor S. and Richardson C. C. (1985) A bacteriophage T7 RNA polymerase/promoter system for controlled exclusive expression of specific genes, Proc. Natl. Acad. Sci. USA 82, 1074-1078).

pT7-7(NS5B) contains the HCV sequence from nucleotide 7590 to nucleotide 9366, and codes for the NS5B protein reported in SEQ ID NO: 1.

In order to obtain this plasmid, a cDNA fragment was generated by PCR using synthetic oligonucleotides having the sequences 5'-TCAATGTCCTACACATGGAC-3' (SEQ ID NO: 10) and 5'-GATCTCTAGATCATCGGTTGGGG-GAGGAGGTAGATGCC-3' (SEQ ID NO: 11), respectively. The PCR product was then treated with the Klenow DNA polymerase, and subsequently ligated in the E. coli expression vector pT7-7 after linearizing it with EcoRI and blunting its estremities with the Klenow DNA polymerase. Alternatively, cDNA fragment was generated by PCR using synthetic oligonucleotides having the sequences 5'-TGTCAATGTC-CTACACATGG-3' (SEQ ID NO: 13) and 5'-AATATTC-GAATTCATCGGTTGGGGAGCAGGTAGATG-3' (SEQ ID NO: 14), respectively. The PCR product was then treated with the Klenow DNA polymerase, and subsequently ligated in the E. coli expression vector pT7-7 after linearizing it with NdeI and blunting its estremities with the Klenow DNA polymerase.

The invention claimed is:

1. A method for identifying a HCV RNA-dependent RNA polymerase inhibitor comprising:
   (a) incubating in vitro a composition comprising a purified HCV NS5B recombinant protein, ribonucleotide substrates, an RNA template, and a test compound, under conditions suitable to produce NS5B RNA-dependent RNA polymerase activity in the absence of said test compound, wherein said recombinant protein was expressed in either a eukaryotic or prokaryotic heterologous system and purified to apparent homogeneity, wherein said NS5B is the only HCV protein present during said incubating; and
   (b) measuring the ability of said test compound to inhibit said NS5B RNA-dependent RNA polymerase activity and thereby identifying an HCV RNA-dependent RNA polymerase inhibitor.

2. The method of claim 1, wherein said method measures primer independent RNA-dependent RNA polymerase activity.

* * * * *

SEQUENCE LISTING

```
<160> NUMBER OF SEQ ID NOS: 14

<210> SEQ ID NO 1
<211> LENGTH: 591
<212> TYPE: PRT
<213> ORGANISM: Hepatitis C virus

<400> SEQUENCE: 1

Ser Met Ser Tyr Thr Trp Thr Gly Ala Leu Ile Thr Pro Cys Ala Ala
 1               5                  10                  15
```

-continued

Glu Glu Ser Lys Leu Pro Ile Asn Ala Leu Ser Asn Ser Leu Leu Arg
            20                  25                  30

His His Asn Met Val Tyr Ala Thr Thr Ser Arg Ser Ala Gly Leu Arg
            35                  40                  45

Gln Lys Lys Val Thr Phe Asp Arg Leu Gln Val Leu Asp Asp His Tyr
        50                  55                  60

Arg Asp Val Leu Lys Glu Met Lys Ala Lys Ala Ser Thr Val Lys Ala
65                  70                  75                  80

Lys Leu Leu Ser Val Glu Glu Ala Cys Lys Leu Thr Pro Pro His Ser
                85                  90                  95

Ala Lys Ser Lys Phe Gly Tyr Gly Ala Lys Asp Val Arg Asn Leu Ser
            100                 105                 110

Ser Lys Ala Val Asn His Ile His Ser Val Trp Lys Asp Leu Leu Glu
            115                 120                 125

Asp Thr Val Thr Pro Ile Asp Thr Thr Ile Met Ala Lys Asn Glu Val
        130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Thr Leu Pro Gln Val Val Met Gly Ser Ser Tyr Gly
            180                 185                 190

Phe Gln Tyr Ser Pro Gly Gln Arg Val Glu Phe Leu Val Asn Thr Trp
            195                 200                 205

Lys Ser Lys Lys Asn Pro Met Gly Phe Ser Tyr Asp Thr Arg Cys Phe
        210                 215                 220

Asp Ser Thr Val Thr Glu Asn Asp Ile Arg Val Glu Glu Ser Ile Tyr
225                 230                 235                 240

Gln Cys Cys Asp Leu Ala Pro Glu Ala Arg Gln Ala Ile Lys Ser Leu
                245                 250                 255

Thr Glu Arg Leu Tyr Ile Gly Gly Pro Leu Thr Asn Ser Lys Gly Gln
            260                 265                 270

Asn Cys Gly Tyr Arg Arg Cys Arg Ala Ser Gly Val Leu Thr Thr Ser
            275                 280                 285

Cys Gly Asn Thr Leu Thr Cys Tyr Leu Lys Ala Ser Ala Ala Cys Arg
        290                 295                 300

Ala Ala Lys Leu Gln Asp Cys Thr Met Leu Val Asn Gly Asp Asp Leu
305                 310                 315                 320

Val Val Ile Cys Glu Ser Ala Gly Thr Gln Glu Asp Ala Ala Ser Leu
                325                 330                 335

Arg Val Phe Thr Glu Ala Met Thr Arg Tyr Ser Ala Pro Pro Gly Asp
            340                 345                 350

Pro Pro Gln Pro Glu Tyr Asp Leu Glu Leu Ile Thr Ser Cys Ser Ser
        355                 360                 365

Asn Val Ser Val Ala His Asp Ala Ser Gly Lys Arg Val Tyr Tyr Leu
            370                 375                 380

Thr Arg Asp Pro Thr Thr Pro Leu Ala Arg Ala Ala Trp Glu Thr Ala
385                 390                 395                 400

Arg His Thr Pro Val Asn Ser Trp Leu Gly Asn Ile Ile Met Tyr Ala
                405                 410                 415

Pro Thr Leu Trp Ala Arg Met Ile Leu Met Thr His Phe Phe Ser Ile
            420                 425                 430

-continued

```
Leu Leu Ala Gln Glu Gln Leu Glu Lys Ala Leu Asp Cys Gln Ile Tyr
        435                 440                 445

Gly Ala Cys Tyr Ser Ile Glu Pro Leu Asp Leu Pro Gln Ile Ile Glu
        450                 455                 460

Arg Leu His Gly Leu Ser Ala Phe Ser Leu His Ser Tyr Ser Pro Gly
465                 470                 475                 480

Glu Ile Asn Arg Val Ala Ser Cys Leu Arg Lys Leu Gly Val Pro Pro
                485                 490                 495

Leu Arg Val Trp Arg His Arg Ala Arg Ser Val Arg Ala Arg Leu Leu
            500                 505                 510

Ser Gln Gly Gly Arg Ala Ala Thr Cys Gly Lys Tyr Leu Phe Asn Trp
        515                 520                 525

Ala Val Lys Thr Lys Leu Lys Leu Thr Pro Ile Pro Ala Ala Ser Arg
        530                 535                 540

Leu Asp Leu Ser Gly Trp Phe Val Ala Gly Tyr Ser Gly Gly Asp Ile
545                 550                 555                 560

Tyr His Ser Leu Ser Arg Ala Arg Pro Arg Trp Phe Met Leu Cys Leu
                565                 570                 575

Leu Leu Leu Ser Val Gly Val Gly Ile Tyr Leu Leu Pro Asn Arg
            580                 585                 590

<210> SEQ ID NO 2
<211> LENGTH: 2201
<212> TYPE: PRT
<213> ORGANISM: cDNA clone pCD (38-9.4)

<400> SEQUENCE: 2

Met Asp Arg Glu Met Ala Ala Ser Cys Gly Gly Ala Val Phe Val Gly
1               5                   10                  15

Leu Val Leu Leu Thr Leu Ser Pro Tyr Tyr Lys Val Phe Leu Ala Arg
            20                  25                  30

Leu Ile Trp Trp Leu Gln Tyr Phe Thr Thr Arg Ala Glu Ala Asp Leu
        35                  40                  45

His Val Trp Ile Pro Pro Leu Asn Ala Arg Gly Gly Arg Asp Ala Ile
    50                  55                  60

Ile Leu Leu Met Cys Ala Val His Pro Glu Leu Ile Phe Asp Ile Thr
65                  70                  75                  80

Lys Leu Leu Ile Ala Ile Leu Gly Pro Leu Met Val Leu Gln Ala Gly
                85                  90                  95

Ile Thr Arg Val Pro Tyr Phe Val Arg Ala Gln Gly Leu Ile His Ala
            100                 105                 110

Cys Met Leu Val Arg Lys Val Ala Gly Gly His Tyr Val Gln Met Ala
        115                 120                 125

Phe Met Lys Leu Gly Ala Leu Thr Gly Thr Tyr Ile Tyr Asn His Leu
    130                 135                 140

Thr Pro Leu Arg Asp Trp Pro Arg Ala Gly Leu Arg Asp Leu Ala Val
145                 150                 155                 160

Ala Val Glu Pro Val Val Phe Ser Asp Met Glu Thr Lys Ile Ile Thr
                165                 170                 175

Trp Gly Ala Asp Thr Ala Ala Cys Gly Asp Ile Ile Leu Gly Leu Pro
            180                 185                 190

Val Ser Ala Arg Arg Gly Lys Glu Ile Leu Leu Gly Pro Ala Asp Ser
        195                 200                 205

Leu Glu Gly Arg Gly Leu Arg Leu Leu Ala Pro Ile Thr Ala Tyr Ser
    210                 215                 220
```

```
Gln Gln Thr Arg Gly Leu Leu Gly Cys Ile Ile Thr Ser Leu Thr Gly
225                 230                 235                 240

Arg Asp Lys Asn Gln Val Glu Gly Glu Val Gln Val Val Ser Thr Ala
            245                 250                 255

Thr Gln Ser Phe Leu Ala Thr Cys Val Asn Gly Val Cys Trp Thr Val
        260                 265                 270

Tyr His Gly Ala Gly Ser Lys Thr Leu Ala Ala Pro Lys Gly Pro Ile
    275                 280                 285

Thr Gln Met Tyr Thr Asn Val Asp Gln Asp Leu Val Gly Trp Pro Lys
290                 295                 300

Pro Pro Gly Ala Arg Ser Leu Thr Pro Cys Thr Cys Gly Ser Ser Asp
305                 310                 315                 320

Leu Tyr Leu Val Thr Arg His Ala Asp Val Ile Pro Val Arg Arg Arg
                325                 330                 335

Gly Asp Ser Arg Gly Ser Leu Leu Ser Pro Arg Pro Val Ser Tyr Leu
            340                 345                 350

Lys Gly Ser Ser Gly Gly Pro Leu Leu Cys Pro Phe Gly His Ala Val
        355                 360                 365

Gly Ile Phe Arg Ala Ala Val Cys Thr Arg Gly Val Ala Lys Ala Val
    370                 375                 380

Asp Phe Val Pro Val Glu Ser Met Glu Thr Thr Met Arg Ser Pro Val
385                 390                 395                 400

Phe Thr Asp Asn Ser Ser Pro Pro Ala Val Pro Gln Ser Phe Gln Val
                405                 410                 415

Ala His Leu His Ala Pro Thr Gly Ser Gly Lys Ser Thr Lys Val Pro
            420                 425                 430

Ala Ala Tyr Ala Ala Gln Gly Tyr Lys Val Leu Val Leu Asn Pro Ser
        435                 440                 445

Val Ala Ala Thr Leu Gly Phe Gly Ala Tyr Met Ser Lys Ala His Gly
    450                 455                 460

Ile Asp Pro Asn Ile Arg Thr Gly Val Arg Thr Ile Thr Thr Gly Ala
465                 470                 475                 480

Pro Val Thr Tyr Ser Thr Tyr Gly Lys Phe Leu Ala Asp Gly Gly Cys
                485                 490                 495

Ser Gly Gly Ala Tyr Asp Ile Ile Ile Cys Asp Glu Cys His Ser Thr
            500                 505                 510

Asp Ser Thr Thr Ile Leu Gly Ile Gly Thr Val Leu Asp Gln Ala Glu
        515                 520                 525

Thr Ala Gly Ala Arg Leu Val Val Leu Ala Thr Ala Thr Pro Pro Gly
    530                 535                 540

Ser Val Thr Val Pro His Pro Asn Ile Glu Glu Val Ala Leu Ser Asn
545                 550                 555                 560

Thr Gly Glu Ile Pro Phe Tyr Gly Lys Ala Ile Pro Ile Glu Ala Ile
                565                 570                 575

Arg Gly Gly Arg His Leu Ile Phe Cys His Ser Lys Lys Cys Asp
            580                 585                 590

Glu Leu Ala Ala Lys Leu Ser Gly Leu Gly Ile Asn Ala Val Ala Tyr
        595                 600                 605

Tyr Arg Gly Leu Asp Val Ser Val Ile Pro Thr Ile Gly Asp Val Val
    610                 615                 620

Val Val Ala Thr Asp Ala Leu Met Thr Gly Tyr Thr Gly Asp Phe Asp
625                 630                 635                 640
```

-continued

Ser Val Ile Asp Cys Asn Thr Cys Val Thr Gln Thr Val Asp Phe Ser
              645                 650                 655

Leu Asp Pro Thr Phe Thr Ile Glu Thr Thr Val Pro Gln Asp Ala
          660                 665                 670

Val Ser Arg Ser Gln Arg Arg Gly Arg Thr Gly Arg Gly Arg Gly
          675                 680                 685

Ile Tyr Arg Phe Val Thr Pro Gly Glu Arg Pro Ser Gly Met Phe Asp
    690                 695                 700

Ser Ser Val Leu Cys Glu Cys Tyr Asp Ala Gly Cys Ala Trp Tyr Glu
705             710                 715                 720

Leu Thr Pro Ala Glu Thr Ser Val Arg Leu Arg Ala Tyr Leu Asn Thr
              725                 730                 735

Pro Gly Leu Pro Val Cys Gln Asp His Leu Glu Phe Trp Glu Ser Val
              740                 745                 750

Phe Thr Gly Leu Thr His Ile Asp Ala His Phe Leu Ser Gln Thr Lys
              755                 760                 765

Gln Ala Gly Asp Asn Phe Pro Tyr Leu Val Ala Tyr Gln Ala Thr Val
770             775                 780

Cys Ala Arg Ala Gln Ala Pro Pro Pro Ser Trp Asp Gln Met Trp Lys
785             790                 795                 800

Cys Leu Ile Arg Leu Lys Pro Thr Leu His Gly Pro Thr Pro Leu Leu
              805                 810                 815

Tyr Arg Leu Gly Ala Val Gln Asn Glu Val Thr Leu Thr His Pro Ile
              820                 825                 830

Thr Lys Tyr Ile Met Ala Cys Met Ser Ala Asp Leu Glu Val Val Thr
          835                 840                 845

Ser Thr Trp Val Leu Val Gly Gly Val Leu Ala Ala Leu Ala Ala Tyr
850                 855                 860

Cys Leu Thr Thr Gly Ser Val Val Ile Val Gly Arg Ile Ile Leu Ser
865                 870                 875                 880

Gly Arg Pro Ala Ile Val Pro Asp Arg Glu Leu Leu Tyr Gln Glu Phe
              885                 890                 895

Asp Glu Met Glu Glu Cys Ala Ser His Leu Pro Tyr Ile Glu Gln Gly
              900                 905                 910

Met Gln Leu Ala Glu Gln Phe Lys Gln Lys Ala Leu Gly Leu Leu Gln
          915                 920                 925

Thr Ala Thr Lys Gln Ala Glu Ala Ala Pro Val Val Glu Ser Lys
          930                 935                 940

Trp Arg Ala Leu Glu Thr Phe Trp Ala Lys His Met Trp Asn Phe Ile
945                 950                 955                 960

Ser Gly Ile Gln Tyr Leu Ala Gly Leu Ser Thr Leu Pro Gly Asn Pro
              965                 970                 975

Ala Ile Ala Ser Leu Met Ala Phe Thr Ala Ser Ile Thr Ser Pro Leu
          980                 985                 990

Thr Thr Gln Ser Thr Leu Leu Phe Asn Ile Leu Gly Gly Trp Val Ala
          995                 1000                1005

Ala Gln Leu Ala Pro Pro Ser Ala Ala Ser Ala Phe Val Gly Ala Gly
          1010                1015                1020

Ile Ala Gly Ala Ala Val Gly Ser Ile Gly Leu Gly Lys Val Leu Val
1025                1030                1035                1040

Asp Ile Leu Ala Gly Tyr Gly Ala Gly Val Ala Gly Ala Leu Val Ala
                  1045                1050                1055

Phe Lys Val Met Ser Gly Glu Met Pro Ser Thr Glu Asp Leu Val Asn

-continued

```
                1060            1065            1070
Leu Leu Pro Ala Ile Leu Ser Pro Gly Ala Leu Val Val Gly Val Val
        1075            1080            1085
Cys Ala Ala Ile Leu Arg Arg His Val Gly Pro Gly Glu Gly Ala Val
        1090            1095            1100
Gln Trp Met Asn Arg Leu Ile Ala Phe Ala Ser Arg Gly Asn His Val
1105            1110            1115            1120
Ser Pro Thr His Tyr Val Pro Glu Ser Asp Ala Ala Arg Val Thr
                1125            1130            1135
Gln Ile Leu Ser Ser Leu Thr Ile Thr Gln Leu Leu Lys Arg Leu His
        1140            1145            1150
Gln Trp Ile Asn Glu Asp Cys Ser Thr Pro Cys Ser Gly Ser Trp Leu
        1155            1160            1165
Arg Asp Val Trp Asp Trp Ile Cys Thr Val Leu Thr Asp Phe Lys Thr
        1170            1175            1180
Trp Leu Gln Ser Lys Leu Leu Pro Gln Leu Pro Gly Val Pro Phe Phe
1185            1190            1195            1200
Ser Cys Gln Arg Gly Tyr Lys Gly Val Trp Arg Gly Asp Gly Ile Met
                1205            1210            1215
Gln Thr Thr Cys Pro Cys Gly Ala Gln Ile Thr Gly His Val Lys Asn
        1220            1225            1230
Gly Ser Met Arg Ile Val Gly Pro Lys Thr Cys Ser Asn Thr Trp His
        1235            1240            1245
Gly Thr Phe Pro Ile Asn Ala Tyr Thr Thr Gly Pro Cys Thr Pro Ser
        1250            1255            1260
Pro Ala Pro Asn Tyr Ser Arg Ala Leu Trp Arg Val Ala Ala Glu Glu
1265            1270            1275            1280
Tyr Val Glu Val Thr Arg Val Gly Asp Phe His Tyr Val Thr Gly Met
                1285            1290            1295
Thr Thr Asp Asn Val Lys Cys Pro Cys Gln Val Pro Ala Pro Glu Phe
        1300            1305            1310
Phe Ser Glu Val Asp Gly Val Arg Leu His Arg Tyr Ala Pro Ala Cys
        1315            1320            1325
Arg Pro Leu Leu Arg Glu Glu Val Thr Phe Gln Val Gly Leu Asn Gln
        1330            1335            1340
Tyr Leu Val Gly Ser Gln Leu Pro Cys Glu Pro Glu Pro Asp Val Ala
1345            1350            1355            1360
Val Leu Thr Ser Met Leu Thr Asp Pro Ser His Ile Thr Ala Glu Thr
                1365            1370            1375
Ala Lys Arg Arg Leu Ala Arg Gly Ser Pro Pro Ser Leu Ala Ser Ser
        1380            1385            1390
Ser Ala Ser Gln Leu Ser Ala Pro Ser Leu Lys Ala Thr Cys Thr Thr
        1395            1400            1405
His His Val Ser Pro Asp Ala Asp Leu Ile Glu Ala Asn Leu Leu Trp
        1410            1415            1420
Arg Gln Glu Met Gly Gly Asn Ile Thr Arg Val Glu Ser Glu Asn Lys
1425            1430            1435            1440
Val Val Val Leu Asp Ser Phe Asp Pro Leu Arg Ala Glu Glu Asp Glu
                1445            1450            1455
Arg Glu Val Ser Val Pro Ala Glu Ile Leu Arg Lys Ser Lys Lys Phe
        1460            1465            1470
Pro Ala Ala Met Pro Ile Trp Ala Arg Pro Asp Tyr Asn Pro Pro Leu
        1475            1480            1485
```

```
Leu Glu Ser Trp Lys Asp Pro Asp Tyr Val Pro Val Val His Gly
        1490                1495                1500
Cys Pro Leu Pro Pro Ile Lys Ala Pro Pro Ile Pro Pro Arg Arg
1505                1510                1515                1520
Lys Arg Thr Val Val Leu Thr Glu Ser Ser Val Ser Ser Ala Leu Ala
                1525                1530                1535
Glu Leu Ala Thr Lys Thr Phe Gly Ser Ser Glu Ser Ser Ala Val Asp
        1540                1545                1550
Ser Gly Thr Ala Thr Ala Leu Pro Asp Gln Ala Ser Asp Asp Gly Asp
        1555                1560                1565
Lys Gly Ser Asp Val Glu Ser Tyr Ser Ser Met Pro Pro Leu Glu Gly
        1570                1575                1580
Glu Pro Gly Asp Pro Asp Leu Ser Asp Gly Ser Trp Ser Thr Val Ser
1585                1590                1595                1600
Glu Glu Ala Ser Glu Asp Val Val Cys Cys Ser Met Ser Tyr Thr Trp
                1605                1610                1615
Thr Gly Ala Leu Ile Thr Pro Cys Ala Ala Glu Glu Ser Lys Leu Pro
        1620                1625                1630
Ile Asn Ala Leu Ser Asn Ser Leu Leu Arg His His Asn Met Val Tyr
        1635                1640                1645
Ala Thr Thr Ser Arg Ser Ala Gly Leu Arg Gln Lys Lys Val Thr Phe
        1650                1655                1660
Asp Arg Leu Gln Val Leu Asp Asp His Tyr Arg Asp Val Leu Lys Glu
1665                1670                1675                1680
Met Lys Ala Lys Ala Ser Thr Val Lys Ala Lys Leu Leu Ser Val Glu
                1685                1690                1695
Glu Ala Cys Lys Leu Thr Pro Pro His Ser Ala Lys Ser Lys Phe Gly
        1700                1705                1710
Tyr Gly Ala Lys Asp Val Arg Asn Leu Ser Ser Lys Ala Val Asn His
        1715                1720                1725
Ile His Ser Val Trp Lys Asp Leu Leu Glu Asp Thr Val Thr Pro Ile
        1730                1735                1740
Asp Thr Thr Ile Met Ala Lys Asn Glu Val Phe Cys Val Gln Pro Glu
1745                1750                1755                1760
Lys Gly Gly Arg Lys Pro Ala Arg Leu Ile Val Phe Pro Asp Leu Gly
                1765                1770                1775
Val Arg Val Cys Glu Lys Met Ala Leu Tyr Asp Val Val Ser Thr Leu
                1780                1785                1790
Pro Gln Val Val Met Gly Ser Ser Tyr Gly Phe Gln Tyr Ser Pro Gly
        1795                1800                1805
Gln Arg Val Glu Phe Leu Val Asn Thr Trp Lys Ser Lys Lys Asn Pro
        1810                1815                1820
Met Gly Phe Ser Tyr Asp Thr Arg Cys Phe Asp Ser Thr Val Thr Glu
1825                1830                1835                1840
Asn Asp Ile Arg Val Glu Glu Ser Ile Tyr Gln Cys Cys Asp Leu Ala
                1845                1850                1855
Pro Glu Ala Arg Gln Ala Ile Lys Ser Leu Thr Glu Arg Leu Tyr Ile
        1860                1865                1870
Gly Gly Pro Leu Thr Asn Ser Lys Gly Gln Asn Cys Gly Tyr Arg Arg
        1875                1880                1885
Cys Arg Ala Ser Gly Val Leu Thr Thr Ser Cys Gly Asn Thr Leu Thr
1890                1895                1900
```

```
Cys Tyr Leu Lys Ala Ser Ala Ala Cys Arg Ala Ala Lys Leu Gln Asp
1905                1910                1915                1920

Cys Thr Met Leu Val Asn Gly Asp Asp Leu Val Val Ile Cys Glu Ser
            1925                1930                1935

Ala Gly Thr Gln Glu Asp Ala Ala Ser Leu Arg Val Phe Thr Glu Ala
        1940                1945                1950

Met Thr Arg Tyr Ser Ala Pro Pro Gly Asp Pro Pro Gln Pro Glu Tyr
    1955                1960                1965

Asp Leu Glu Leu Ile Thr Ser Cys Ser Ser Asn Val Ser Val Ala His
1970                1975                1980

Asp Ala Ser Gly Lys Arg Val Tyr Tyr Leu Thr Arg Asp Pro Thr Thr
1985                1990                1995                2000

Pro Leu Ala Arg Ala Ala Trp Glu Thr Ala Arg His Thr Pro Val Asn
            2005                2010                2015

Ser Trp Leu Gly Asn Ile Ile Met Tyr Ala Pro Thr Leu Trp Ala Arg
        2020                2025                2030

Met Ile Leu Met Thr His Phe Phe Ser Ile Leu Leu Ala Gln Glu Gln
    2035                2040                2045

Leu Glu Lys Ala Leu Asp Cys Gln Ile Tyr Gly Ala Cys Tyr Ser Ile
2050                2055                2060

Glu Pro Leu Asp Leu Pro Gln Ile Ile Glu Arg Leu His Gly Leu Ser
2065                2070                2075                2080

Ala Phe Ser Leu His Ser Tyr Ser Pro Gly Glu Ile Asn Arg Val Ala
            2085                2090                2095

Ser Cys Leu Arg Lys Leu Gly Val Pro Pro Leu Arg Val Trp Arg His
        2100                2105                2110

Arg Ala Arg Ser Val Arg Ala Arg Leu Leu Ser Gln Gly Gly Arg Ala
    2115                2120                2125

Ala Thr Cys Gly Lys Tyr Leu Phe Asn Trp Ala Val Lys Thr Lys Leu
2130                2135                2140

Lys Leu Thr Pro Ile Pro Ala Ala Ser Arg Leu Asp Leu Ser Gly Trp
2145                2150                2155                2160

Phe Val Ala Gly Tyr Ser Gly Gly Asp Ile Tyr His Ser Leu Ser Arg
            2165                2170                2175

Ala Arg Pro Arg Trp Phe Met Leu Cys Leu Leu Leu Leu Ser Val Gly
        2180                2185                2190

Val Gly Ile Tyr Leu Leu Pro Asn Arg
    2195                2200

<210> SEQ ID NO 3
<211> LENGTH: 26
<212> TYPE: DNA
<213> ORGANISM: Oligonucleotide synthesizer

<400> SEQUENCE: 3
gccgagatgc catcttcaaa cagttc                                          26

<210> SEQ ID NO 4
<211> LENGTH: 24
<212> TYPE: DNA
<213> ORGANISM: Oligonucleotide synthesizer

<400> SEQUENCE: 4
gtgtacaaca aggtccatat cacc                                            24

<210> SEQ ID NO 5
```

```
<211> LENGTH: 24
<212> TYPE: DNA
<213> ORGANISM: Oligonucleotide synthesizer

<400> SEQUENCE: 5
ggtctttctg aacgggatat aaac                                              24

<210> SEQ ID NO 6
<211> LENGTH: 31
<212> TYPE: DNA
<213> ORGANISM: Oligonucleotide synthesizer

<400> SEQUENCE: 6
aaggatccat gtcaatgtcc tacacatgga c                                      31

<210> SEQ ID NO 7
<211> LENGTH: 36
<212> TYPE: DNA
<213> ORGANISM: Oligonucleotide synthesizer

<400> SEQUENCE: 7
aatattcgaa ttcatcggtt ggggagcagg tagatg                                 36

<210> SEQ ID NO 8
<211> LENGTH: 22
<212> TYPE: DNA
<213> ORGANISM: Oligonucleotide synthesizer

<400> SEQUENCE: 8
tggctggcaa ggcacacagg ct                                                22

<210> SEQ ID NO 9
<211> LENGTH: 20
<212> TYPE: DNA
<213> ORGANISM: Oligonucleotide synthesizer

<400> SEQUENCE: 9
aggcagggta gatctatgtc                                                   20

<210> SEQ ID NO 10
<211> LENGTH: 20
<212> TYPE: DNA
<213> ORGANISM: Oligonucleotide synthesizer

<400> SEQUENCE: 10
tcaatgtcct acacatggac                                                   20

<210> SEQ ID NO 11
<211> LENGTH: 38
<212> TYPE: DNA
<213> ORGANISM: Oligonucleotide synthesizer

<400> SEQUENCE: 11
gatctctaga tcatcggttg ggggaggagg tagatgcc                               38

<210> SEQ ID NO 12
<211> LENGTH: 399
<212> TYPE: RNA
<213> ORGANISM: Rattus norvegicus

<400> SEQUENCE: 12
gggagaccac aacgguuucc cucuagaaau aauuuuguuu aacuuuaaga aggagauaua       60
cauauggcua gaauucgcgc ccuggcuggc aaggcacaca ggcugagugc ugaggaacgg      120
```

-continued

```
gaccagcugc ugccaaaccu gcgggccgug ggguggaaug aacuggaagg ccgagaugcc      180
aucuucaaac aguuccauuu uaaagacuuc aacagggcuu uuggcuucau gacaagaguc      240
gcccugcagg cugaaaagcu ggaccaccau cccgaguggu uuaacgugua caacaagguc      300
cauaucaccu ugagcaccca cgaaugugcc ggucuuucug aacgggauau aaaccuggcc      360
agcuucaucg aacaaguugc cgugucuaug acauagauc                             399

<210> SEQ ID NO 13
<211> LENGTH: 20
<212> TYPE: DNA
<213> ORGANISM: Oligonucleotide synthesizer

<400> SEQUENCE: 13
tgtcaatgtc ctacacatgg                                                   20

<210> SEQ ID NO 14
<211> LENGTH: 36
<212> TYPE: DNA
<213> ORGANISM: Oligonucleotide synthesizer

<400> SEQUENCE: 14
aatattcgaa ttcatcggtt ggggagcagg tagatg                                36
```